US008492572B2

(12) United States Patent
Klingberg et al.

(10) Patent No.: US 8,492,572 B2
(45) Date of Patent: Jul. 23, 2013

(54) LIQUID FATTY AMINE CARBOXYLATE SALT COMPOSITION

(75) Inventors: Anders Klingberg, Henån (SE); Magnus Svensson, Stenungsund (SE)

(73) Assignee: Akzo Nobel Chemicals International B.V., Arnhem (NL)

( * ) Notice: Subject to any disclaimer, the term of this patent is extended or adjusted under 35 U.S.C. 154(b) by 67 days.

(21) Appl. No.: 13/376,748

(22) PCT Filed: Jun. 15, 2010

(86) PCT No.: PCT/EP2010/058340

§ 371 (c)(1), (2), (4) Date: Dec. 21, 2011

(87) PCT Pub. No.: WO2010/146030

PCT Pub. Date: Dec. 23, 2010

(65) Prior Publication Data

US 2012/0116107 A1 May 10, 2012

Related U.S. Application Data

(60) Provisional application No. 61/218,231, filed on Jun. 18, 2009.

(30) Foreign Application Priority Data

Jun. 18, 2009 (EP) .................................... 09163035

(51) Int. Cl.
*C07C 229/00* (2006.01)

(52) U.S. Cl.
USPC .......................................................... 554/104

(58) Field of Classification Search
USPC .......................................................... 554/104
See application file for complete search history.

(56) References Cited

U.S. PATENT DOCUMENTS

| | | | |
|---|---|---|---|
| 2,816,870 | A | 12/1957 | Lentz et al. |
| 2,891,012 | A | 6/1959 | Lentz et al. |
| 2,891,392 | A | 6/1959 | Wildhaber |
| 4,591,447 | A | 5/1986 | Kubala |
| 4,695,389 | A | 9/1987 | Kubala |
| 5,182,035 | A | 1/1993 | Schmidt et al. |
| 5,474,692 | A | 12/1995 | Laufenberg et al. |
| 5,500,137 | A | 3/1996 | Bacon et al. |
| 6,569,822 | B1 | 5/2003 | Guillemet |
| 2006/0046940 | A1 | 3/2006 | Almalki et al. |

FOREIGN PATENT DOCUMENTS

| | | | |
|---|---|---|---|
| DE | 197 21 602 | A1 | 11/1998 |
| EP | 0 011 515 | A1 | 5/1980 |
| EP | 0 372 628 | A2 | 6/1990 |
| EP | 0 623 666 | A1 | 11/1994 |
| EP | 0011515 | A * | 5/2008 |
| WO | WO 94/32562 | | 2/1994 |
| WO | WO98/53033 | | 11/1998 |

OTHER PUBLICATIONS

European Search Report for Application No. 09163035.0; Completion date May 17, 2010.
International Search Report for PCT Application No. PCT/EP2010/058340; Completion date Jul. 27, 2010.
English Abstract of EP 0 011 515 A1, 2010.
English Abstract of EP 0 623 666 A1, 2010.

* cited by examiner

*Primary Examiner* — Deborah D Carr
(74) *Attorney, Agent, or Firm* — Sugiarto Hadikusumo

(57) ABSTRACT

A composition comprising 40 to 90 wt % of at least one fatty amine carboxylate salt, water, and the carboxylic acid corresponding to said carboxylate is provided. In the composition, the weight:weight ratio of carboxylic acid:water is in the range of from 20:1 to 1:1. The inventive compositions have a pour point at a temperature of below 30° C.

15 Claims, No Drawings

LIQUID FATTY AMINE CARBOXYLATE SALT COMPOSITION

CROSS-REFERENCES TO RELATED APPLICATIONS

This application is a National Stage entry of International Application PCT/EP2010/058340, filed Jun. 15, 2010, which claims the benefit of U.S. Patent Application No. 61/218,231, filed Jun. 18, 2009, and European Patent Application No. 09163035.0, filed Jun. 18, 2009. The contents of the aforementioned applications are incorporated herein by reference in their entireties.

FIELD OF THE INVENTION

The present invention relates to compositions comprising fatty amine carboxylate salt, the carboxylic acid corresponding to the carboxylate and water, which compositions have a pour point of at most 30° C. The present invention also relates to the use of a carboxylic acid and water to prepare a fatty amine carboxylate composition of the present invention, and to methods for the preparation of compositions of the present invention.

TECHNICAL BACKGROUND

Fatty amine carboxylate salts, such as fatty amine acetate salts, are common surface active compounds used in many applications.

However, one problem of this class of compounds is that they are solid, non-pourable products at room temperature and often up to about 45° C. or higher, leading to handling problems. The fatty amine carboxylate has to be either melted and poured out from a drum or dug out by hand from the drum.

Further, due to health aspects, handling of solid fatty amine carboxylate salts requires the use of protection masks and protective clothes to protect one self against particles, dust and vapors.

Exposure to the fatty amine carboxylate salts during handling could be avoided if the fatty amine carboxylate salts could exist in liquid form, enabling pouring or pumping of the compound.

Liquid tallow diamine diacetate salts are currently available under the trademark Duomac T36 (available from Akzo Nobel Surface Chemistry AB, Sweden), containing 40% of the tallow diamine diacetate salt dissolved in butyleneglycol and water.

U.S. Pat. No. 6,569,822 relates to a concentrated liquid compositions of fatty diamine acetate salts by using alcohol, water and at least one dissolving agent solvent, where the ratio of fatty diamine acetate salt:dissolving agent solvent is less than or equal to 4:1.

However, both the alcohol and the dissolving agent solvent represent highly flammable compounds.

There exists thus a need in the art for highly concentrated fatty amine carboxylate compositions that do not, or contain only small amounts of, flammable solvents.

SUMMARY OF THE INVENTION

One object of the invention is to at least partly overcome the drawbacks of the prior art, and to provide alternative high concentrated liquid fatty amine carboxylate salt compositions with high stability of the amines.

It is another object of the present invention to provide high concentrated liquid fatty amine carboxylate salt compositions with reduced content of flammable solvents.

The inventors have now surprisingly found that these objects can be met by using water and the carboxylic acid corresponding to the carboxylate as a means to liquefy fatty amine carboxylate salts at low temperatures.

Fatty amine carboxylate salts dissolved within certain ranges of water and the carboxylic acid has surprisingly been found to be liquid at room temperature and below, even for high concentrations of fatty amine carboxylate salts.

Hence, in a first aspect, the present invention relates to a composition comprising 40 to 90 wt % of at least one fatty amine carboxylate salt, water, and the carboxylic acid corresponding to said carboxylate. In the composition, the weight:weight ratio of carboxylic acid:water is in the range of from 20:1 to 1:1. Further, the composition has a pour point at a temperature of below 30° C.

Even though fatty amine carboxylate salts have high melting temperatures, typically above 45° C., they can be contained in a room temperature pourable composition, at high carboxylate content, due to the use of water and the carboxylic acid corresponding to the carboxylate as a solvent.

Further, the water content in the compositions of the invention reduces the formation of amides which normally occurs in mixtures of fatty amine carboxylates and carboxylic acids.

In a second aspect, the present invention relates to the use of a carboxylic acid and water in a weight ratio of from 20:1 to 1:1 as an additive to a fatty amine carboxylate of said carboxylic acid, to obtain a composition according to the present invention, such as comprising 40 to 90 wt % of said fatty amine carboxylate, which composition has a pour point at a temperature of ≦30° C.

In a third aspect, the present invention relates to a method for the production of a fatty amine carboxylate composition having a pour point of ≦30° C., comprising providing a fatty amine or carboxylate thereof; and mixing said fatty amine or carboxylate thereof with said carboxylic acid corresponding to said carboxylate and water, resulting in a composition of the present invention.

It is to be noted that the present invention relates to all possible combinations of the appended claims.

These above aspects will be described more in detail in the following detailed description on the invention.

DETAILED DESCRIPTION OF THE INVENTION

The present invention is based on the finding that within certain ranges, fatty amine carboxylate salts mixed with water and the carboxylic acid corresponding to the carboxylate form a liquid composition at about room temperature, even at high concentrations of the fatty amine carboxylate in the composition.

Hence, a composition of the invention comprises a fatty amine carboxylate salt, water and the carboxylic acid corresponding to the carboxylate, and has a pour point of ≦30° C., such as ≦20° C., for example ≦10° C.

As used herein, the terms "a carboxylic acid corresponding to a carboxylate", "a carboxylate corresponding to a carboxylic acid" and related terms refers to that the carboxylic acid is the protonated carboxylate. As an illustration: should the fatty amine carboxylate salt used in the invention be fatty amine acetate, the corresponding carboxylic acid is acetic acid. Should the fatty amine carboxylate salt be a fatty amine propionate, the corresponding carboxylic acid is propionic acid.

As used herein, the term "pour point" defines the temperature at which a solid composition turns into a pourable composition. In this context, a composition is especially regarded as pourable when the viscosity is below 500 mPa*s (cP) at a shear rate of 20 $s^{-1}$, as measured on a Bohlin VOR Rheometer equipped with a C14 measurement system. For the measurement, a 20 g*$cm^{-1}$ torque bar and a bob/cup was used. In order to reach the desired temperature, the formulation was allowed to stand in the cup for 10 minutes before start of measurement. A shear rate sweep was made from 1 to 119 $s^{-1}$ without pre-shearing of the sample. From the viscosity measurements the conclusion could be drawn that if a composition had a viscosity of below 500 mPa*s (cP) at a shear rate of 20 $s^{-1}$, the composition was considered as being pourable.

The fatty amine carboxylate salt concentration should be in the range of from about 40 wt %, such as from about 50 wt %, for example from about 60 wt %, to about 90 wt %, such as to about 85 wt %, for example to about 70 wt %.

Unless otherwise explicitly mentioned, all percentages mentioned herein refer to weight %, based on the total weight of the composition.

In addition to the fatty amine carboxylate salt, the corresponding carboxylic acid and water typically represents the major part of the composition. The carboxylic acid:water ratio in the composition is typically from about 20:1 to about 1:1. In embodiments of the invention, the carboxylic acid: water ratio is from about 19:1 to about 6:4, such as from about 6:1 to 2:1.

The use of carboxylic acid and water in the ratio mentioned above as an additive to a fatty amine carboxylate of said carboxylic acid, to obtain a composition of the present invention is to be contemplated as a separate aspect of the invention. In embodiments, carboxylic acid and water in the ratio mentioned above is used as a solvent for the fatty amine carboxylate. A solution of the fatty amine carboxylate salt in carboxylic acid and water is typically an essentially clear liquid.

Unless otherwise mentioned, all ratios between two compounds refer to weight:weight ratios.

In embodiments, a composition of the present invention may be a liquid solution at temperatures below said pour point. In such cases, at 30° C. and possibly at lower temperatures, the composition is in the form of a solution where the fatty amine carboxylate is dissolved in the corresponding carboxylic acid and water based solvent, forming an essentially clear liquid. A clear liquid is often preferred over a non-clear liquid due to reduced risk for precipitation or phase separation.

Should the water content in the composition be too high, fatty amine carboxylate salt compositions have been shown to form a gel. In gel form, the composition is not pourable. Hence, the water content is chosen low enough to avoid this gelling. The water content is typically below about 20%, such as below about 10%, for example below 5%.

Should no water be present, the melting temperature of the composition has been shown not to be significantly lower than the melting temperature of the fatty amine carboxylate it self. Hence, the water content is typically at least 1%, such as at least 2%.

Further, it has been shown that in presence of a carboxylic acid, fatty amines and fatty amine carboxylates is subject to amide formation. The introduction of water in the composition has been shown to reduce such amide formation.

The composition may optionally comprise additional solvents in addition to water and the carboxylic acid. Such additional solvents are typically comprised in a ratio of additional solvent:fatty amine acetate of from 0:1 to 2:9, for example below 1:10. However, it is to be noted that the compositions of the invention does not need to contain any such additional solvents at all. Examples of such additional solvents include conventional organic solvents, including but not limited to alcohols, for example isopropanol, ethyleneglycol, propyleneglycol, butylene glycol and di(ethyleneglycol), ethers and ketones. The content of additional solvents is typically kept low enough not to yield a composition that is flammable at room temperature.

The fatty amine carboxylate, as such, typically has a melting point/pour point of well above 30° C. Hence, in embodiments of the present invention, the fatty acid carboxylates contemplated for use are such fatty acid carboxylates having a melting point/pour point of above 30° C., such as above 45° C., for example above 60° C. Data regarding the pour point or melting point of commercially available fatty amine carboxylates can inter alia be retrieved from the MSDS sheets issued in connection to such products.

As used in the present specification, the term "fatty amine" typically relates to monoamines, diamines and polyamines of the formula I $$R^1—NH—(R^2—NH)_nH \qquad (I),$$

where $R^1$ is selected from straight and branched, saturated and unsaturated $C_{6-30}$ hydrocarbyl groups; $R^2$ is $(CH_2)_x$ where x is 2-6; and n is an integer from 0 to 4.

In embodiments of the present invention, $R^1$ is a straight or branched, saturated or unsaturated $C_{8-22}$ hydrocarbyl. Examples of $R^1$-groups include, but are not limited to coco alkyl, oleyl and tallow alkyl, rapeseed alkyl, soya alkyl, hexadecyl, tetradecyl, and mixtures thereof, and other fatty hydrocarbyl groups of vegetable or animal origin.

Examples of $R^2$-groups include, but are not limited to ethylene, propylene, butylene, pentylene and hexylene. Typically, $R^2$ is propylene, i.e. x is 3.

Typically, n is 0 (monoamine) or 1 (diamine).

As used in the present specification, the term "fatty amine carboxylate" relates to the carboxylic acid salt of a fatty amine. The carboxylate salt of a fatty diamine is typically a dicarboxylate salt.

The carboxylic acids contemplated for use in the present invention includes, but are not limited to carboxylic acids of the formula $R^3—COOH$, where $R^3$ is a linear, branched or cyclic $C_{1-6}$ hydrocarbyl group, especially a linear or branched $C_{1-5}$ alkyl group. Acetic acid and propionic acid, and their corresponding carboxylates, i.e. acetates and propionates, respectively, are especially contemplated.

The following fatty amines were used in the below described experiments: Duomeen® T: N-Tallow-1,3-diaminopropane; Armeen® C: Coco-amine; and Armeen® HT: Hydrogenated tallow-amine, all from Akzo Nobel Surface Chemistry AB, Sweden.

Duomeen® T was neutralized with 357 mg/g of acetic acid (HAc) (99.8%) to obtain the diacetate form, herein denoted Duomac T. Duomac T has a melting point of 82° C.

Armeen® C was neutralized with 294 mg/g HAc to obtain the acetate form, herein denoted Armac C. Armac C has a melting point interval of 45-60° C.

Armeen® HT was neutralized with 221 mg/g HAc to obtain the acetate form, herein denoted Armac HT Armac HT has a melting point of 60° C.

Duomeen® T was neutralized with 441 mg/g propionic acid (99.7%) to obtain the di-propionate form, herein denoted Duoprop T. Duoprop T is solid at 30° C.

Experiment 1

Physical Form of Fatty Amine Carboxylates

The fatty amine was heated to liquid form and added to the carboxylic acid, to form a composition of fatty amine carboxylate and carboxylic acid. Water was added in indicated amounts to obtain the desired compositions. The final compositions were filled in 10 ml glass flasks and the flasks were closed with screw caps. The formulations were agitated with a magnetic stirrer for about 15 minutes and if necessary to get a clear formulation, heated to 30 to 40° C. The total weight of each sample was 10 g.

After mixing, the samples were stored in a freezer over night and then stored at 10° C., 20° C. and 30° C. respectively.

The physical form of the samples was determined at the times noted in the tables below by ocular examination and by turning the flask upside down.

TABLE 1

Physical form of Armac HT + HAc + $H_2O$

| Sample | Armac HT (%) | HAc (%) | $H_2O$ (%) | 24 h @ 10° C. | 48 h @ 10° C. | 24 h @ 20° C. | 48 h @ 20° C. | 24 h @ 30° C. | 48 h @ 30° C. |
|---|---|---|---|---|---|---|---|---|---|
| 1 | 60 | 40 | 0 | Solid, not clear | Solid, not clear | Solid, not clear | Solid, not clear | Solid, not clear | Solid, not clear |
| 2 | 60 | 38 | 2 | Solid, not clear | Solid, not clear | Solid, not clear | Solid, not clear | Liquid, not clear | Liquid, not clear |
| 3 | 60 | 36 | 4 | Solid, not clear | Solid, not clear | Solid, not clear | Solid, not clear | Liquid, not clear | Liquid, not clear |
| 4 | 60 | 34 | 6 | Solid, not clear | Solid, not clear | Solid, not clear | Solid, not clear | Liquid, not clear | Liquid, not clear |
| 5 | 60 | 32 | 8 | Solid, not clear | Solid, not clear | Solid, not clear | Solid, not clear | Liquid, not clear | Liquid, not clear |
| 6 | 60 | 30 | 10 | Solid, not clear | Solid, not clear | Solid, not clear | Solid, not clear | Liquid, starts to clear | Liquid, not clear |
| 7 | 60 | 28 | 12 | Solid, not clear | Solid, not clear | Solid, not clear | Solid, not clear | Liquid, starts to clear | Liquid, not clear |
| 8 | 60 | 26 | 14 | Solid, not clear | Solid, not clear | Solid, not clear | Solid, not clear | Liquid, starts to clear | Liquid, not clear |
| 9 | 60 | 24 | 16 | Solid, not clear | Solid, not clear | Solid, not clear | Solid, not clear | Liquid, starts to clear | Liquid, not clear |
| 10 | 60 | 20 | 20 | Solid, not clear | Solid, not clear | Solid, not clear | Solid, not clear | Solid, not clear | Solid, not clear |
| 11 | 60 | 15 | 25 | Solid, not clear | Solid, not clear | Solid, not clear | Solid, not clear | Solid, not clear | Solid, not clear |
| 12 | 80 | 20 | 0 | Solid, not clear | Solid, not clear | Solid, not clear | Solid, not clear | Solid, not clear | Solid, not clear |
| 13 | 80 | 10 | 10 | Solid, not clear | Solid, not clear | Solid, not clear | Solid, not clear | Solid, not clear | Solid, not clear |
| 14 | 80 | 4 | 16 | Solid, not clear | Solid, not clear | Solid, not clear | Solid, not clear | Solid, not clear | Solid, not clear |
| 15 | 40 | 60 | 0 | Liquid, not clear | Liquid, not clear | Liquid, not clear | Liquid, not clear | Liquid, not clear | Liquid, not clear |
| 16 | 40 | 56 | 4 | Liquid, not clear | Liquid, not clear | Liquid, not clear | Liquid, not clear | Liquid, not clear | Liquid, not clear |
| 17 | 40 | 52 | 8 | Liquid, not clear | Liquid, not clear | Liquid, not clear | Liquid, not clear | Liquid, not clear | Liquid, not clear |
| 18 | 40 | 48 | 12 | Liquid, not clear | Liquid, not clear | Liquid, not clear | Liquid, not clear | Liquid, not clear | Liquid, not clear |
| 19 | 40 | 44 | 16 | Liquid, not clear | Liquid, not clear | Liquid, not clear | Liquid, not clear | Liquid, not clear | Liquid, not clear |

Samples 2 to 9 and 13 to 15 are according to the invention

TABLE 2

Physical form of Duomac T + HAc + $H_2O$

| Sample | Duomac HT (%) | HAc (%) | $H_2O$ (%) | 24 h @ 10° C. | 48 h @ 10° C. | 24 h @ 20° C. | 48 h @ 20° C. | 24 h @ 30° C. | 48 h @ 30° C. |
|---|---|---|---|---|---|---|---|---|---|
| 20 | 60 | 34 | 6 | Solid, not clear | Solid, not clear | Liquid, high visc, not clear | Liquid, high visc, starts to clear | Liquid, clear | Liquid, clear |
| 21 | 60 | 32 | 8 | Liquid, high viscosity, not clear | Liquid, high visc, not clear | Liquid, clear | Liquid, clear | Liquid, clear | Liquid, clear |
| 22 | 60 | 30 | 10 | Liquid, clear | Liquid, clear | Liquid, clear | Liquid, clear | Liquid, clear | Liquid, clear |
| 23 | 60 | 28 | 12 | Liquid clear | Liquid, clear | Liquid, clear | Liquid, clear | Liquid, clear | Liquid, clear |
| 24 | 60 | 26 | 14 | Clear, Jelly | Clear, Jelly | Clear, Jelly | Clear, Jelly | Liquid, clear | Liquid, clear |
| 25 | 60 | 24 | 16 | Clear, Jelly | Clear, Jelly | Clear, Jelly | Clear, Jelly | Clear, Jelly | Clear, Jelly |
| 26 | 80 | 20 | 0 | Solid, not clear | Solid, not clear | Solid, not clear | Solid, not clear | Solid, not clear | Solid, not clear |
| 27 | 80 | 18 | 2 | Solid, not clear | Solid, not clear | Solid, not clear | Solid, not clear | Solid, not clear | Solid, not clear |
| 28 | 80 | 16 | 4 | Solid, not clear | Solid, not clear | Solid, not clear | Solid, not clear | Liquid, clear | Liquid, clear |
| 29 | 80 | 14 | 6 | Solid, not clear | Solid, not clear | Solid, not clear | Solid, not clear | Solid, not clear | Solid, not clear |
| 30 | 70 | 20 | 10 | Solid, not clear | Solid, not clear | Clear, Jelly | Clear, Jelly | Clear, Jelly | Clear, Jelly |
| 31 | 70 | 18 | 12 | Solid, not clear | Solid, not clear | Liquid, clear | Liquid, Clear | Liquid, Clear | Liquid, Clear |

Samples 20-24, 28 and 31 are according to the invention

TABLE 3

Physical form of Armac C + HAc + $H_2O$

| Sample | Armac C (%) | HAc (%) | $H_2O$ (%) | 24 h @ 10° C. | 48 h @ 10° C. | 24 h @ 20° C. | 48 h @ 20° C. | 24 h @ 30° C. | 48 h @ 30° C. |
|---|---|---|---|---|---|---|---|---|---|
| 32 | 60 | 40 | 0 | Liquid, clear | Liquid, clear | Liquid, clear | Liquid, clear | Liquid, clear | Liquid, clear |
| 33 | 60 | 38 | 2 | Liquid, clear | Liquid, clear | Liquid, clear | Liquid, clear | Liquid, clear | Liquid, clear |
| 34 | 60 | 36 | 4 | Liquid, clear | Liquid, clear | Liquid, clear | Liquid, clear | Liquid, clear | Liquid, clear |
| 35 | 60 | 34 | 6 | Liquid, clear | Liquid, clear | Liquid, clear | Liquid, clear | Liquid, clear | Liquid, clear |
| 36 | 60 | 32 | 8 | Liquid, clear | Liquid, clear | Liquid, clear | Liquid, clear | Liquid, clear | Liquid, clear |
| 37 | 60 | 30 | 10 | Liquid, clear | Liquid, clear | Liquid, clear | Liquid, clear | Liquid, clear | Liquid, clear |
| 38 | 60 | 28 | 12 | Liquid, clear | Liquid, clear | Liquid, clear | Liquid, clear | Liquid, clear | Liquid, clear |
| 39 | 60 | 26 | 14 | Liquid, clear | Liquid, clear | Liquid, clear | Liquid, clear | Liquid, clear | Liquid, clear |
| 40 | 60 | 24 | 16 | Liquid, clear | Liquid, clear | Liquid, clear | Liquid, clear | Liquid, clear | Liquid, clear |

TABLE 3-continued

Physical form of Armac C + HAc + $H_2O$

| Sample | Armac C (%) | HAc (%) | $H_2O$ (%) | 24 h @ 10° C. | 48 h @ 10° C. | 24 h @ 20° C. | 48 h @ 20° C. | 24 h @ 30° C. | 48 h @ 30° C. |
|---|---|---|---|---|---|---|---|---|---|
| 41 | 80 | 20 | 0 | Solid, not clear | High visc, starts to clear | Liquid, clear | Liquid, clear | Liquid, clear | Liquid, clear |
| 42 | 80 | 18 | 2 | Liquid, clear | Liquid, clear | Liquid, clear | Liquid, clear | Liquid, clear | Liquid, clear |
| 43 | 80 | 16 | 4 | Liquid, clear | Liquid, clear | Liquid, clear | Liquid, clear | Liquid, clear | Liquid, clear |
| 44 | 80 | 14 | 6 | Liquid, clear | Liquid, clear | Liquid, clear | Liquid, clear | Liquid, clear | Liquid, clear |
| 45 | 80 | 12 | 8 | Solid, not clear | High visc, starts to clear | High visc, starts to clear | High visc, starts to clear | High visc, starts to clear | High visc, starts to clear |

Samples 33-40, 42-45 are according to the invention

TABLE 4

Physical form of Armac C + HAc + $H_2O$

| Sample | Armac C (%) | HAc (%) | $H_2O$ (%) | 24 h @ 10° C. | 48 h @ 10° C. | 110 h @ 20° C. | 24 h @ 30° C. | 96 h @ 30° C. |
|---|---|---|---|---|---|---|---|---|
| 46 | 85 | 15 | 0 | Solid, not clear | Solid, not clear | Solid, not clear | High visc, starts to clear | High visc, starts to clear |
| 47 | 85 | 11 | 4 | Solid, not clear | Solid, not clear | Liquid, clear | Liquid, clear | Liquid, clear |
| 48 | 85 | 7 | 8 | Solid, not clear | Solid, not clear | Clear, Jelly | Clear, Jelly | Clear, Jelly |
| 49 | 85 | 3 | 12 | Solid, not clear | Solid, not clear | Clear, Jelly | Clear, Jelly | Clear, Jelly |

Sample 47 is according to the invention

TABLE 5

Physical form of Duoprop T + propionic acid + $H_2O$

| Sample | Duoprop T (%) | HPr (%) | $H_2O$ (%) | 24 h @ 10° C. | 48 h @ 10° C. | 24 h @ 20° C. | 48 h @ 20° C. |
|---|---|---|---|---|---|---|---|
| 50 | 60 | 40 | 0 | Liquid, not clear | Liquid, not clear | Liquid, not clear | Liquid, not clear |
| 51 | 60 | 30 | 10 | Liquid, clear | Liquid, clear | Liquid, clear | Liquid, clear |
| 52 | 60 | 20 | 20 | Liquid, clear | Liquid, clear | Liquid, clear | Liquid, clear |
| 53 | 80 | 20 | 0 | Solid, not clear | Solid, not clear | Solid, not clear | Solid, not clear |
| 54 | 80 | 15 | 5 | Solid, not clear | Solid, not clear | Liquid, not clear | Liquid not clear |
| 55 | 80 | 10 | 10 | Jelly, not clear | Jelly, not clear | Jelly, not clear | Jelly, not clear |

Samples 51, 52 and 54 are according to the invention

Experiment 2

Stability of Fatty Acid Acetates

During long term storage, especially at ambient or slightly increased temperatures and acidic pH, fatty amine acetates react to form fatty amides.

In this experiment, four Duomac® T compositions A, B, C and D were tested in respect of their stability against amide formation. Each of the compositions was stored in closed vials at 20° C., 30° C. and 40° C. respectively, and the amine content relative to the amine content in the freshly prepared compositions were determined at 40 and 98 days of storage. The amine content was determined by means of titration with hydrochloric acid.

TABLE 6

| Sample/ storage temperature | Duomac T (%) | HAc | $H_2O$ | % remaining amine N @ 40 days | % remaining amine N @ 98 days |
|---|---|---|---|---|---|
| A/20° C. | 56 | 40 | 4 | 99.5 | 99.2 |
| A/30° C. | 56 | 40 | 4 | 98.7 | 97.5 |
| A/40° C. | 56 | 40 | 4 | 96.8 | 94.6 |
| B/20° C. | 65 | 30 | 5 | 99.4 | 99.0 |

TABLE 6-continued

| Sample/ storage temperature | Duomac T (%) | HAc | $H_2O$ | % remaining amine N @ 40 days | % remaining amine N @ 98 days |
|---|---|---|---|---|---|
| B/30° C. | 65 | 30 | 5 | 97.7 | 97.3 |
| B/40° C. | 65 | 30 | 5 | 96.1 | 93.9 |
| C/20° C. | 70 | 30 | 0 | 99.6 | 99.7 |
| C/30° C. | 70 | 30 | 0 | 97.6 | 97.9 |
| C/40° C. | 70 | 30 | 0 | 93.4 | 90.8 |
| D/20° C. | 60 | 40 | 0 | 99.5 | 99.2 |
| D/30° C. | 60 | 40 | 0 | 98.0 | 96.9 |
| D/40° C. | 60 | 40 | 0 | 95.3 | 92.8 |

From the storage data at 40° C., it is clear that the samples A and B, which contains water, are superior in stability when compared to the samples C and D, which do not contain any water.

The invention claimed is:

1. A composition comprising 40 to 90 wt % of at least one fatty amine carboxylate salt water; and the carboxylic acid corresponding to said carboxylate wherein the weight:weight ratio of carboxylic acid:water is in the range of from 20:1 to 1:1; and said composition has a pour point at a temperature of ≦30° C.

2. The composition according to claim 1, wherein said carboxylic acid is selected from the group consisting of acetic acid and propionic acid.

3. The composition according to claim 1, having a viscosity of at most 500 mPa*s at a shear rate of 20 $s^{-1}$, as measured on a Bohlin VOR Rheometer equipped with a C14 measurement system, at said pour point.

4. The composition according to claim 1, wherein the weight:weight ratio of carboxylic acid:water is from about 19:1 to about 6:4.

5. The composition according to claim 1, comprising from about 1 to about 20 wt % of water.

6. The composition according to claim 1, comprising from about 8 to about 56 wt % of carboxylic acid.

7. The composition according to claim 1, further comprising an additional solvent present at a weight ratio additional solvent:fatty amine carboxylate salt of from 0:1 to 2:9.

8. The composition according to claim 1, said composition being a clear liquid solution at a temperature of ≦30° C.

9. The composition according to claim 1, wherein said fatty amine carboxylate salt component has a melting temperature of at least 45°.

10. The composition according to claim 1, wherein said fatty amine is of the formula (I), $$R^1—NH—(R^2—NH)_nH \qquad (I)$$

where $R^1$ is selected from straight and branched, saturated and unsaturated $C_{6-30}$ hydrocarbyl groups;

$R^2$ is a group $(CH_2)_x$ where x is an integer in the range of 2 to 6; and n is an integer in the range of 0 to 4.

11. The composition according to claim 10, wherein x is 3.

12. The composition according to claim 10 wherein n is 0 or 1.

13. A method for the production of a fatty amine carboxylate salt composition having a pour point of ≦30° C., comprising:

providing a fatty amine or carboxylate salt thereof; and mixing said fatty amine or carboxylate salt thereof with said carboxylic acid corresponding to said carboxylate and water, resulting in a composition comprising 40 to 90 wt % of a fatty amine carboxylate salt water; and the carboxylic acid corresponding to said carboxylate the weight:weight ratio of carboxylic acid:water being in the range of from 20:1 to 1:1, said composition having a pour point of ≦30° C.

14. The method according to claim 13, wherein said fatty amine or fatty amine carboxylate is mixed with said carboxylic acid and thereafter mixed with water.

15. Method of obtaining a composition comprising 40 to 90 wt % of a fatty amine carboxylate salt, the method comprising adding a carboxylic acid and water in a weight ratio of from 20:1 to 1:1 to said fatty amine carboxylate salt of said carboxylic acid, wherein the composition has a pour point at a temperature of ≦30° C.

* * * * *